US006638569B2

(12) United States Patent
McLaughlin et al.

(10) Patent No.: US 6,638,569 B2
(45) Date of Patent: Oct. 28, 2003

(54) APPARATUS AND METHOD FOR COATING SUBSTRATES WITH VACUUM DEPOSITABLE MATERIALS

(76) Inventors: James Andrew McLaughlin, 49 North Parade, Belfast, BT8 2GH, Northern Ireland (GB); John McCune Anderson, Torgrange, Holywood, County Down BT18, ONG, Northern Ireland (GB); Paul Damian Maguire, 139 Cliftonville Road, Belfast, BT14, Northern Ireland (GB)

(*) Notice: Subject to any disclaimer, the term of this patent is extended or adjusted under 35 U.S.C. 154(b) by 0 days.

(21) Appl. No.: 09/893,732

(22) Filed: Jun. 25, 2001

(65) Prior Publication Data

US 2002/0026899 A1 Mar. 7, 2002

Related U.S. Application Data

(63) Continuation of application No. 09/340,094, filed on Jun. 25, 1999, now abandoned.

(51) Int. Cl.$^7$ ............................................. C23C 16/32
(52) U.S. Cl. ............................... 427/249.3; 427/249.7; 427/570
(58) Field of Search ............................ 118/718, 723 E; 427/249.7, 249.3, 570

(56) References Cited

U.S. PATENT DOCUMENTS

| 4,389,970 A | | 6/1983 | Edgerton ................. 118/666 |
| 4,663,183 A | * | 5/1987 | Ovshinsky et al. ......... 427/577 |
| 4,829,189 A | | 5/1989 | Goto et al. ............... 250/492.3 |
| 5,437,725 A | | 8/1995 | Schuster et al. ............ 118/718 |
| 5,464,667 A | | 11/1995 | Kohler et al. .............. 427/577 |
| 5,652,029 A | | 7/1997 | Itoh .......................... 427/569 |
| 5,888,594 A | | 3/1999 | David et al. ............... 427/577 |
| 5,965,216 A | * | 10/1999 | Neuberger et al. ......... 427/577 |

FOREIGN PATENT DOCUMENTS

EP   0 818 801 A2   1/1998

OTHER PUBLICATIONS

Kenji Yamamota et al.—Hard Carbon Film—Feb. 21, 1987.

\* cited by examiner

*Primary Examiner*—Richard Booth
(74) *Attorney, Agent, or Firm*—Mintz, Levin, Cohn, Ferris, Glovsky and Popeo, P.C.

(57) ABSTRACT

An apparatus for coating a substrate with a diamond like coating or other vacuum depositable material comprises a chamber 11 having, or acting as, an anode, means for supporting a substrate 15 in the chamber, means for establishing a low pressure atmosphere containing a hydrocarbon-based gas in the chamber, and a radio frequency source 12 for establishing a gas plasma in the chamber, the substrate 15 acting as a cathode.

13 Claims, 1 Drawing Sheet

APPARATUS AND METHOD FOR COATING SUBSTRATES WITH VACUUM DEPOSITABLE MATERIALS

RELATED APPLICATIONS

This application is a continuation of U.S. Pat. application Ser. No. 09/340,094, filed, Jun. 25, 1999 and now abandoned, which claims priority to Irish Patent Application S980520, filed Jun. 26, 1998.

FIELD OF THE INVENTION

This invention relates to an apparatus and a method for coating diamond like carbon (DLC) or other vacuum depositable material onto a substrate.

BACKGROUND OF THE INVENTION

DLC films or coatings is the generic term for a mixture of $sp^2$ and $sp^3$ bonded carbon and can generally be described as hard, amorphous, lubricious, impermeable, chemically inert and possessing high electrical resistivity proportions.

Presently medical device coatings such as polytetrafluoroethylene (PTFE) or Silicone overlays are applied by dip coating or electrostatic spraying methods thus forming a 200–300 μm thick outer layer. Traditionally these coating techniques have associated problems including poor metal to polymer adhesion and non uniformity of coating. The nature of these coating techniques leads to poor process control due to the fluid dynamics of thick films, poor yields due to adhesion and poor uniformity and large non-environmentally friendly waste.

The most commonly used technique for coating guide wires is electrostatic spraying which gives rise to non-uniform coatings and requires the need for interlayers between the substrate and coating to achieve acceptable adhesion. Additionally excessively thick coatings subsequently adds rigidity to the substrate which may be, for example, a wire or a spring. Furthermore the process gives rise to loosely bonded aspirates which are not acceptable where the substrate is designed for internal use such as medical devices for body implantation.

Thus, for example, medical grade stainless steel guide wires are currently used to aid the introduction of catheters and other medical devices into the human body. The device in a coated or uncoated state must exhibit good flexibility, low surface roughness, possess a high chemical resistance and conform to biocompatibility standards. The device requires surface hardness as it has to be threaded through a metal needle; high flexibility and low surface coefficient of friction in order to aid the movement through channels in the body; and good biocompatibility properties due to the nature of the in vivo procedure.

In the prior art, and with reference to FIG. 1 of the drawings, plasma based coating systems, such as sputtering, and normal RF plasma enhanced chemical vapour deposition chambers, employ the use of parallel plate or conical facing electrodes that only allow 'in the plane of sight' coating. Thus rotation of the substrate is required. Thus in the case of, for example, sputtering, in FIG. 1, the substrate 1 is interposed between two plates 2, 3 in a chamber having walls 5. The plate 2 acts as a cathode; the plate 3 acts as an anode or the walls 5 act as an anode. A source of radio frequency voltage is provided from a source 4. Apart from the need to rotate the substrate 1 relative to the plates 2,3, the coating of the substrate is uneven, non-uniform and non-conformal. This is particularly the case where the surface of the substrate is, at the microscopic level, uneven.

SUMMARY OF THE INVENTION

It is an object of the present invention to provide an apparatus for applying a conformal DLC coating, or other vacuum depositable material, to a substrate.

The invention, therefore, provides an apparatus for coating a substrate with a diamond like coating or other vacuum depositable material, the apparatus comprising a chamber having an anode, means for supporting a substrate in the chamber, means for establishing a low pressure gaseous atmosphere in the chamber, and a radio frequency source for establishing a gas plasma in the chamber, the substrate acting as a cathode.

The invention further provides a method for coating a substrate with a diamond like coating or other vacuum depositable material, the method comprising supporting a substrate in a chamber having an anode, establishing a low pressure gaseous atmosphere in the chamber, and establishing a gas plasma in the chamber using a radio frequency source, the substrate acting as a cathode.

By providing an apparatus in which the substrate is the cathode and the wall or preferably walls of the chamber function as the anode, the substrate may remain static, i.e. rotation of the substrate is not required in order to uniformly coat the substrate. This is particularly advantageous where the substrate comprises, in the microscopic sense, a rough surface. Alternatively, the anode may comprise a plate inside the chamber or may comprise a tubular element in the chamber and into which element the substrate is placed. Instead of using a tubular element, a pair of oppositely disposed hemispherically shaped elements could act as an anode. As a further alternative, the chamber itself could be tubularly shaped in which the curved wall is an anode. In use, a coaxial plasma can form between the cathode and the anode electrode arrangements that are spaced typically over ranges of between 2 cm and 30 cm although this gap can be larger or smaller. The geometry of the anode electrode may be circular or square but in the case of a short gap of the order of a few cms it is preferred, for a conformal coating, that the anode is circular. In the case of a wide gap i.e. greater than 10 cm the geometry of the anode is less important and a square/rectangular arrangement can be utilised due to the nature of electric field confinement over larger distances on small diameter substrates.

BRIEF DESCRIPTION OF THE DRAWINGS

The invention will be understood in greater detail from the following description of the preferred embodiments thereof by way of example only in which.

DETAILED DESCRIPTION OF THE INVENTION

Figure 1:
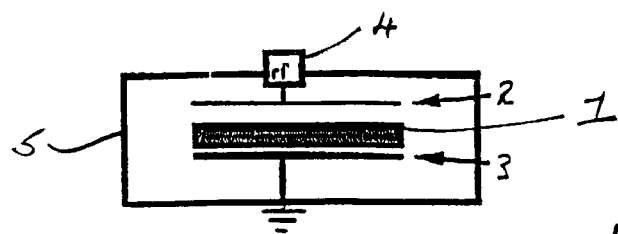
FIG. 1 is a schematic view of a prior art apparatus.
Figure 2:
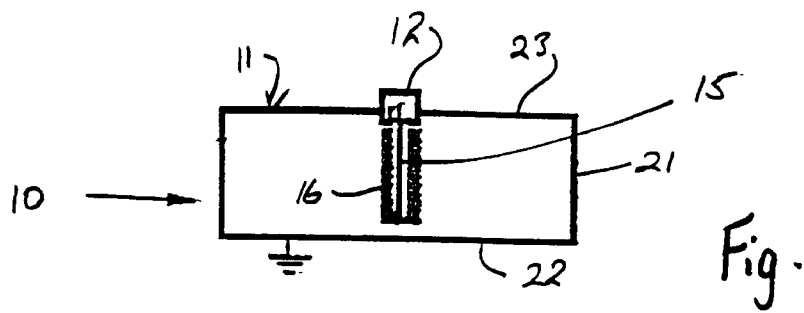
FIG. 2 is a schematic view of a first embodiment of an apparatus according to the invention.
Figure 3:
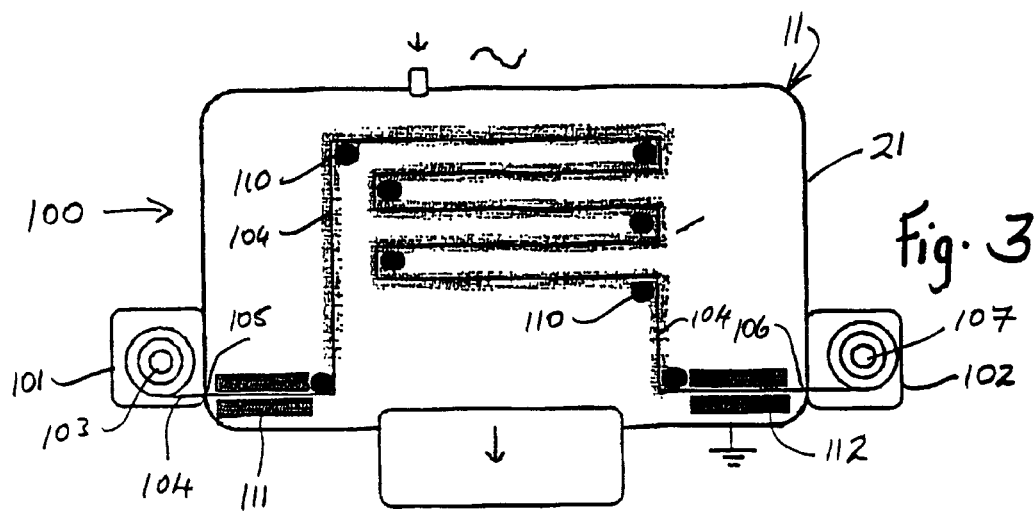
FIG. 3 is a schematic view of a second embodiment of an apparatus according to the invention.

Referring now to FIGS. 2–3 of the drawings and in particular to FIG. 2 thereof, there is shown a first embodiment of an apparatus 10 according to the invention which comprises a chamber 11 having walls 21, a base 22 and a top 23. Associated with the chamber is a radio frequency source 12. An opening (not shown) is provided to enable a gas or gas mixture to be introduced into the chamber. Such a gas mixture is preferably Argon/acetylene or any other hydrocarbon based gas in a preferred ratio of 1:3 If desired, a silicon based gas may also be introduced in which case the ratio is preferably Argon:Acetyene:Silicon based gas=1:3:2. The working pressure of the gas or gas mixture within the chamber is preferably between about 1.06 Pa–1.33 Pa (8–10 mT). The radio frequency is typically about 13.56 MHz giving rise to a self bias DC voltage of about 450V. The power density is typically about 1 to 10 W/cm$^2$.

A substrate 15 is introduced into the chamber 11. In the present embodiment the substrate is in the form of an electrically conductive guide wire, but it could be a conductive tube. The guide wire is connected to the cathode terminal of the electrical source. At least one of the walls 21 and preferably all the walls 21 are connected to the electrically anode (earthed) side of the electrical source. Thus, the wall or walls 21 can function as a anode while the substrate 15 functions as an cathode. An Example of the process condition applicable to the apparatus 10 is:

| | |
|---|---|
| Gas Ratios | Argon:1/Acetyene:3/Silicon based gas:2 |
| Working Pressure | 1.33 Pa (10 mT) |
| Film Thickness | 0.5 μm (Surface roughness >10 nm) |
| Film Thickness | 0.1 μm (Surface roughness <10 nm) |
| Power density | 1 W/cm$^2$ |
| Self DC bias | −450 Volts |

This arrangement will allow for a conformal coating on a conductive substrate having a wide range of geometrical shapes such as spring wound guide wires whereby the interstices are uniformly coated which is unlike the thick and uneven film coatings of the prior art. Where the substrate 15 is a guide wire, a uniform and conformal film coating as obtained in the present invention will provide a smoother passage for the guide wire when in use. The hydrocarbon based gas is ionised within the plasma allowing a range of positively and negatively charged species to be obtained. The positively charged ions are attracted to the cathode and cause controlled ultra thin film growth due to condensation on the substrate. The invention allows optimisation of this growth mechanism due to the particular characteristics such as high plasma densities that arise from the co-axial plasma arrangement and the high rate of surface modification occurring prior and during film deposition. Films as thick as 2 microns can be grown with high hardness and low stresses.

As will be observed, rotation of the substrate is not required in order to provide a uniform coating. Substrate heating to improve adhesion of the sample is not required and deposition takes place at room temperatures, unlike the other plasma based designs mentioned. The invention as illustrated will apply a RF voltage to the electrically conductive substrate 15 allowing it to set a potential difference across a gap (defined by the debye length) thus allowing a co-axial plasma 16 to form. The large DC bias (typically about 450 volts) is provided thereby allowing a high control of film deposition and thus film quality. The nature of the plasma 16 will be unique to this configuration as it will have the ability to conformally surround the substrate 15. This in turn means that uniform coating of a rough surface is possible and the nature of the co-axial plasma gives rise to highly dense plasma phases. The apparatus 10 has the ability to produce ultra-thin or thick conformal films of DLC with hardness, adhesion and low coefficient of friction values much better than those found in prior art planar electrode coating systems, electrostatic or dip coating technologies. The ability to produce ultra thin forms of DLC using the coaxial technique allows low stress coatings which will not de-laminate during elongation of the wire or device.

The present invention ensures that loosely bonded contamination is eliminated and wetability of the surface of the substrate 15 is improved. A plasma polymerised polymeric layer is deposited in order to promote the adhesion of the DLC layer and allow the formation of a graded interface with subsequent layers, although this is not always necessary. Because high density co-axial electrical fields surround the substrate 15, a focused field subsequently gives rise to a focusing effect on the trajectory of the incoming bombarding ions at the cathode. This will produce a deposition process that will have a higher deposition rate and more energetic ion bombardment of the substrate will occur. This will have the effect of higher hardness, higher adhesion and lower surface coefficients of friction due to the ability to former higher levels of sp$^3$ carbon. As a result, a high quality growth mechanism is achieved, more normally associated with high temperature processing.

An acetylene and argon gas mix at 0.266 Pa [2 mT] allows high adhesion (>400 kg/cm$^2$) coatings to be achieved at high deposition rates (>10 μm/hr) with no substrate heating. A dense plasma with high energies allows high adhesion without substrate heating.

It is possible to provide a composite DLC structure throughout the film in conjunction with other elements such as Silicon, Fluorine, Chlorine. The DLC composites provided by the invention allow for much improved adhesion on multiple substrates, as well as dramatically improved surface properties. Contact angles greater than 100° have been established with Si based DLC composites and thermal stability as high as 500° C. can be achieved allowing high temperature annealing of structures. Medical devices such as catheters, medical wires, guide wires, heart valves, vascular grafts, stimulation/sensing electrodes, biosensors and associated packaging as well as many other applications, will all benefit in numerous ways by improving their surface-body fluid interfaces (see Table 1). However it is well established that the wide range of functionality required for today's medical devices requires composite approaches if biocompatability and desired mechanical or electrical properties are to be selectively achieved. Specific surface coatings as thin as 50 nm will exhibit enhanced surface properties such as hard and low coefficient parameters.

Critical to the coatings process is the need for ultra-thin (≦50 nm) highly uniform and conformal layers that have high bond strengths to the underlying substrates. The invention provides a process wherein device surfaces are plasma modified by highly ionised gaseous species whereby surface energy and chemical functionality is dramatically altered allowing optimal thin film coating structures to be deposited with high degrees of substrate bonding. Typically ultra-thin (≦50 nm) adhesion promotion layers can also be utilised and graded into the functional coating. A wide range of materials provide this role such as SiO$_2$ chromium, silica and some plasma polymerised polymers. This phenomenon of grading thin film DLC by adjusting gas flows is one of the key aspects provided by the invention and most suitable to conformal PECVD co-axial coatings. The ultra thin nature of the film will achieve low film stresses due to structural interface matching and bulk relaxation thus improving the coatings lifetime.

The invention outlined so far allows numerous medical devices such as wire based structures to be mounted in the chamber and subsequently coated batch by batch. The main improvement on current techniques is the improved yield, reproducability and coating quality benefits.

However, an alternative mass production technique would be to spool/reel to reel coat. Reference should now be made to FIG. 3 of the drawings. An apparatus 100 comprises a chamber 11 and walls 21 as described with respect to the apparatus 10. Located externally of the chamber 11 is a first housing 101 and a second housing 102. The first housing 101 contains a reel 103 of uncoated guide wire material 104. An opening 105 in the chamber 11 is provided which enables the wire 104 to have access thereto from the housing 101. Similarly, on the opposite side of the chamber 11, an opening 106 is provided which enables coated guide wire to pass from the chamber 11 to the housing 102 and on a take up reel 107. A suitable motor (not shown) provides drive for the take up reel 107.

At various locations inside the chamber 11, there is provided a plurality of guide wheels 110 around which the guide wire 104 is threaded in serpentine fashion. Between the first guide wheel upstream of the plurality of guide wheels 110 and the opening 105, the guide wire 104 passes between a first shield 111 which prevents a plasma developing around the guide wire 104. Similarly, between the last guide wheel and the opening 106, the guide wire 104 passes between a second shield 112 which prevents a plasma developing around the guide wire 104. The guide wheels 110 provide electrical connection to the guide wire 104 thereby enabling the guide wire 104 to act as an cathode with the walls of the chamber 11 acting as the anode.

By providing openings 105, 106 which are relatively small and ensuring that the housings 101, 102 are subject to the same pressures as the chamber 11, continuous coating of a relatively long length of wire 104 is enabled. Because of the insulating nature even at high frequencies of thick layers of DLC at intervals, the process allows for an oxygen plasma in order to try to etch the surrounding walls. This is necessary in order to maintain and electric field and the hydrocarbon based plasma. The guide wire 104 moves preferably at about 6 cm·s$^{-1}$. An example of the process conditions are as follows:

| | |
|---|---|
| Gas Ratios | Argon:1/Acetyene:3 |
| Working Pressure | 1.33 Pa (10 mT) |
| Film Thickness | 0.5 μm (Surface roughness >10 nm) |
| Power density | 1 W/cm$^2$ |
| Self DC bias | −450 Volts |

The invention provides a diamond like carbon thin (DLC) film coating which will provide enhanced bio-functionality in the areas of barrier resistance, low coefficient of friction properties (lubricity), bulk and surface inertness, low stress, insulating, wear resistance, biocompatability, enhanced coating adhesion, conformal coating thickness, high uniformity of coating, increases flexibility of device, decreased electrostatics over other inert coatings and the ability to process a colour change in the coated layer.

Critical to ultrathin coatings is low stress, good stoichiometry, high uniformity and high adhesion. In order to tailor wear and lubricity properties, material parameters, such as surface crystallography and roughness, are important values to monitor and it has been shown that there is a direct relationship to device performance. The invention has the ability to bulk and surface tailor the bio-functionality of a medical device.

The DLC films (a mixture of sp$^3$ and sp$^2$ bonded carbon), are generally hard, amorphous, lubricious, impermeable, chemically inert and with high electrical resistivity/ breakdown strength. Recently in vitro studies have been carried out to investigate the biocompatibility of diamond- like carbon (DLC) coatings. Cell viability measurements have shown no evidence of overt oytotoxicity and or abnormal cellular morphology. Examples of surface modifications properties are provided in Table 1.

TABLE 1

| Surface Modification: Material Property | Analysis | Functional Benefits | Typical Devices |
|---|---|---|---|
| Metallic Coating Noble Metals and Alloys | EDX, SPCS and SEM and AC Impedance | X-ray opaque, Biocidal activity of silver, and electrical electrode for stimulation and sensing | Catheter, Pacemekers Electrodes and radio opaque markers |
| Ceramic and DLC | Cyclovaltometry, EDX, XPS and SEM and AC Impedance | Wear, Barrier resistance, electrical insulator, hard wear, inertness and biactive (porous ceramic) | Catheters, needles electrodes invivo sensors guide wires, pacemakers, anti infection coatings on polymer tubing |
| Surface Roughness | AEM, Stylus, Optical | Decreases lubricity and higher surface energy | Catheters, needles, electrodes invivo, sensors guide wires, pacemakers |
| Coating Thickness | AFM, Xray, Reflectometry, Elipsometry | Decrease coating stress. Less traumatic and increased flexibility | Balloons, functional stimulation electrodes, catheters with small lumen |
| Coefficient of Friction | Static and dynamic tests | Less insertion trauma and reported less infection | Catheters, needles, electrodes invivo, sensors guide wires, pacemakers |
| Adhesion | Z-Axis pull tester | Improved adhesion with no delamination therefore longer product life. | All devices where coating is required |
| Wear | Pin on disc | Longer life | All devices where coating is required |
| Hardness | Nanoindention | Scratch and puncture resistance | Balloons, guide wires, needles, rotor blades etc. |
| Inert | Cyclovoltometry | No leaching and stable electrical potentials and electrode/tissue interfaces | On metal and polymer products where ionic leaching is a problem and implant electrodes |
| Barrier Coating | AC Impedance | Low corrosion | On metal and polymer products where ionia leaching, corrosion and water permeability is a problem e.g., optical sensing |
| BioFilm Resistant | OWLS, Bio-fouling tests | Improved biocompatability and improved active device performance | In vivo sensors, smart cathetes, stents, tracts respiratory tubing etc, |

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A method for coating a substrate in the form of an elongated body with a vacuum depositable material, the method comprising supporting the substrate inside a vacuum chamber adjacent to an anode, connecting the substrate as a cathode, introducing a gas of depositable material at low pressure into the vacuum chamber, and connecting an RF source across the anode and the substrate to produce a coaxial electric field surrounding the substrate, the electric field ionising the gas to generate a corresponding plasma likewise coaxially surrounding the substrate, where the depositable material is coated on all sides of the substrate.

2. The method of claim 1, wherein the anode comprises at least one wall of the vacuum chamber.

3. The method of claim 1, wherein the substrate is wire.

4. The method of claim 1, wherein the substrate is conductive tubing.

5. The method of claim 1, wherein the substrate is maintained at room temperature.

6. The method of claim 1, wherein the gas comprises a hydrocarbon-based gas to coat the substrate with diamond-like carbon.

7. The method of claim 6, wherein the hydrocarbon-based gas is acetylene.

8. The method of claim 6, wherein the hydrocarbon-based gas is mixed with an inert gas.

9. The method of claim 8, wherein the inert gas is argon.

10. The method of claim 8, wherein the inert gas is silicon-based.

11. The method of claim 1, wherein the low pressure is between about 1.06Pa–1.33Pa (8–10 mT).

12. The method of claim 1, wherein the substrate is not rotated in the chamber.

13. The method of claim 11, wherein the anode is tubular.

* * * * *